United States Patent
Hreha et al.

(10) Patent No.: US 10,501,578 B1
(45) Date of Patent: Dec. 10, 2019

(54) BIS-SCHIFF BASE COMPOSITIONS AND FORMULATIONS

(71) Applicant: Jalapeno Holdings, LLC, Bellbrook, OH (US)

(72) Inventors: Richard D. Hreha, Dayton, OH (US); Tat H. Tong, Bellbrook, OH (US)

(73) Assignee: Jalapeno Holdings, LLC, Bellbrook, OH (US)

( * ) Notice: Subject to any disclaimer, the term of this patent is extended or adjusted under 35 U.S.C. 154(b) by 0 days.

(21) Appl. No.: 15/440,829

(22) Filed: Feb. 23, 2017

Related U.S. Application Data

(60) Provisional application No. 62/298,504, filed on Feb. 23, 2016.

(51) Int. Cl.
  *C08G 73/00* (2006.01)
  *C07D 307/34* (2006.01)

(52) U.S. Cl.
  CPC ............ *C08G 73/00* (2013.01); *C07D 307/34* (2013.01)

(58) Field of Classification Search
  CPC .................................................... C08G 73/00
  See application file for complete search history.

(56) References Cited

U.S. PATENT DOCUMENTS 3,945,999 A * 3/1976 Gruffaz ................. G03C 1/675
                                                    549/472
2015/0376153 A1* 12/2015 Masuno ............... C07D 307/52
                                                    549/506

FOREIGN PATENT DOCUMENTS

CN      104193706 B   *  4/2014   ........... C07D 307/52
JP      06-271558     * 12/1994   ........... C07D 307/52

OTHER PUBLICATIONS

Wen et al. (Synthetic Metals 202 (2015) 89-97).*
Ali et al. (Spectrochinnica Acta Part A: Molecular and Biomolecular Spectroscopy 132 (2014) 52-60).*
Enein et al. (Journal of Thermal Analysis and Calorimetry, vol. 91 (2008) 3, 929-936).*
Zhizaho et al. (Organometallics 2013, 32, 3611-3617).*
Brunovska et al., "Thermal Properties of Phthalonitrile Functional Polybenzoxazines", Thermochemica Acta Aug. 2000: 195-203.

(Continued)

Primary Examiner — Shane Fang
(74) Attorney, Agent, or Firm — Dinsmore & Shohl LLP

(57) ABSTRACT

Chemical compositions are provided having the structure of Formula (I):

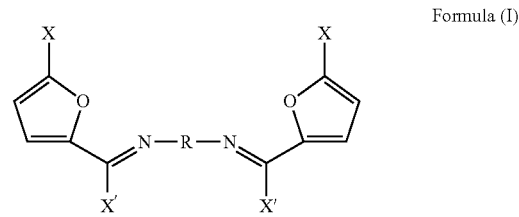

Formula (I)

where R includes at least one aromatic moiety, and X and X' may both or independently include an aromatic moiety, an aliphatic moiety, or a hydrogen. Additionally, chemical formulations are provided which include the chemical composition having the structure of Formula (I) and at least one solvent.

11 Claims, 4 Drawing Sheets

(56) References Cited

OTHER PUBLICATIONS

"Game Changing Development Program, Potential Industry/NASA Partnership in the Development and Assessment of High Performance Thermal Protection System Materials", NNH15ZOA005L. Mar. 2, 2015. NSPIRES. Jul. 3, 2015.

Ahmed et al., "Thermal insulation by heat resistant polymers for solid rocket motor insulation", Journal of Composite Materials 46(13) pp. 1549-1559, 2011.

De Almedia et al., "Processing and characterization of ablative composites used in rock motors", Journal of Reinforced Plastics & Composites, vol. 33(16) pp. 1474-1484, 2014.

Natali et al., "Ablative properties of carbon black and MWNT/phenolic composites: A comparative study", Composites: Part A 43, pp. 174-182, 2012.

Ogasawara et al., "Thermal Response and Ablation Characteristics of Carbon Fiber Reinforced Composite with Novel Silicon Containing Polymer MSP", Journal of Composite Materials, vol. 36, No. 2, pp. 143-157, 2002.

Parkar et al., "Ablation characteristics of an aromatic thermosetting copolyester/carbon fiber composite", Journal of Composite Materials, 46(15), pp. 1819-1830, 2011.

Sabagh et al., "Thermochemical erosion and thermophysical properties of phenolic resin/carbon fiber/graphite nanocomposites", Journal of Reinforced Plastics & Composites, vol. 35(24), pp. 1814-1825, 2016.

Sandor, "PBI (Polybenzimidazole): Synthesis, Properties and Applications", High Performance Polymers, vol. 2, No. 1, pp. 25-37, 1990.

Williams et al., "Thermal Protection Materials: Thermophysical Property Data", NASA Reference Publication 1289, 1992.

Zhang et al., "Addition-curable phthalonitrile-functionalized novolac resin", High Performance Polymers, 24(5), pp. 398-404, 2012.

\* cited by examiner

BIS-SCHIFF BASE COMPOSITIONS AND FORMULATIONS

CROSS-REFERENCE TO RELATED APPLICATIONS

This application claims priority to U.S. Provisional Application 62/298,504, filed Feb. 23, 2016, which is incorporated by reference herein in its entirety.

FIELD OF INVENTION

Embodiments of the present disclosure generally relate to bis-Schiff base compositions and chemical formulations that include a bis-Schiff base composition and a solvent. More specifically, embodiments of the present disclosure relate to bis-Schiff base compositions and formulations with improved melt viscosity and stability.

BACKGROUND

Schiff bases, named after Nobel Prize winner Hugo Schiff, are compounds having the general structure $R_2C=NR'$. A bis-Schiff base refers to a compound having at least two Schiff base components in the compound. Schiff bases are known to be useful intermediates in making catalysts, dyes, and polymers for wide variety of photochemical, electronic, opto-electronic, and photonic applications.

Conventional chemical processes to make bis-Schiff base compositions, such as bis-Schiff resins or its related polymer products, involve large quantities of organic solvent during synthesis and often require the use of catalysts and/or other polymerizable functional groups. Moreover, the processes often have multiple steps and laborious purification processes. Bis-Schiff bases having epoxy functionalities may require additional curing agents and mixing processes to properly cure. As such, Schiff bases are not typically economically viable as a resin product for the large-scale production of polymers or polymer composites.

Additionally, bis-Schiff bases of aliphatic aldehydes are readily polymerizable and unstable. Bis-Schiff bases of aromatic aldehydes and aromatic amines are more stable, but more difficult to process, particularly for those with polyaromatic moieties, due to their higher melting points. When bis-Schiff base compositions are used as liquid resins, for instance, in molding or coating processes, the compositions must have viscosities that are malleable enough to manipulate. Typically, the composition would be heated until the appropriate viscosity was achieved, and the resin would be applied on a mold or a substrate. However, conventional bis-Schiff bases may begin to undergo further reactions, polymerizing and/or crosslinking when in a melted state due to their high melting point. This results in rapid increases in viscosity and gelation that prevent the resin from being processed into the desirable product form and shape.

SUMMARY

Accordingly, a need exists for bis-Schiff compositions with improved rheology, such as a sufficiently low melt viscosity, that remain relatively stable within a workable time and temperature processing window to allow the resin to be processed into a product form without further undesirable reactions occurring.

The present embodiments address these needs by providing chemical compositions, polymers produced from the chemical compositions, and chemical formulations with a much larger time and temperature processing window with desirably low viscosities. As used herein, "melt viscosity" refers to the measurement of the flow of a melted material, which may be measured based on the resistance to deformation as a function of shear rate or stress with dependence on time and temperature.

Embodiments of the present disclosure relate to chemical compositions having the structure of Formula (I):

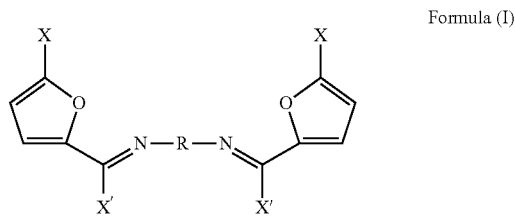

Formula (I)

where R comprises at least one aromatic moiety, and X and X' may both or independently comprise aromatic moieties, aliphatic moieties, or a hydrogen. The chemical composition may be a neat polymerizable resin. As used herein, a "neat resin" refers to a resin that contains only the main identified monomers or polymers with minimal amounts or without stabilizers or additives.

Further embodiments of the present disclosure relate to polymers produced from the chemical composition having the structure of Formula (I):

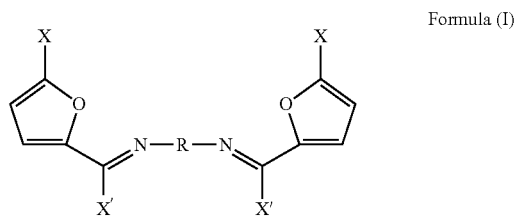

Formula (I)

where R comprises at least one aromatic moiety, and X and X' may both or independently comprise aromatic moieties, aliphatic moieties, or a hydrogen.

Additional embodiments of the present disclosure relate to chemical formulations having a component having the structure of Formula (I):

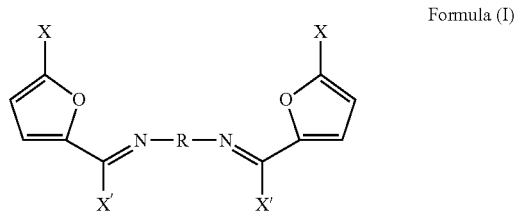

Formula (I)

wherein R comprises at least one aromatic moiety, and X and X' may both or independently comprise aromatic moieties, aliphatic moieties, or a hydrogen; and at least one solvent.

BRIEF DESCRIPTION OF THE DRAWINGS

The following detailed description of specific embodiments of the present disclosure can be best understood when read in conjunction with the following drawings, in which.

DETAILED DESCRIPTION

Figure 1:
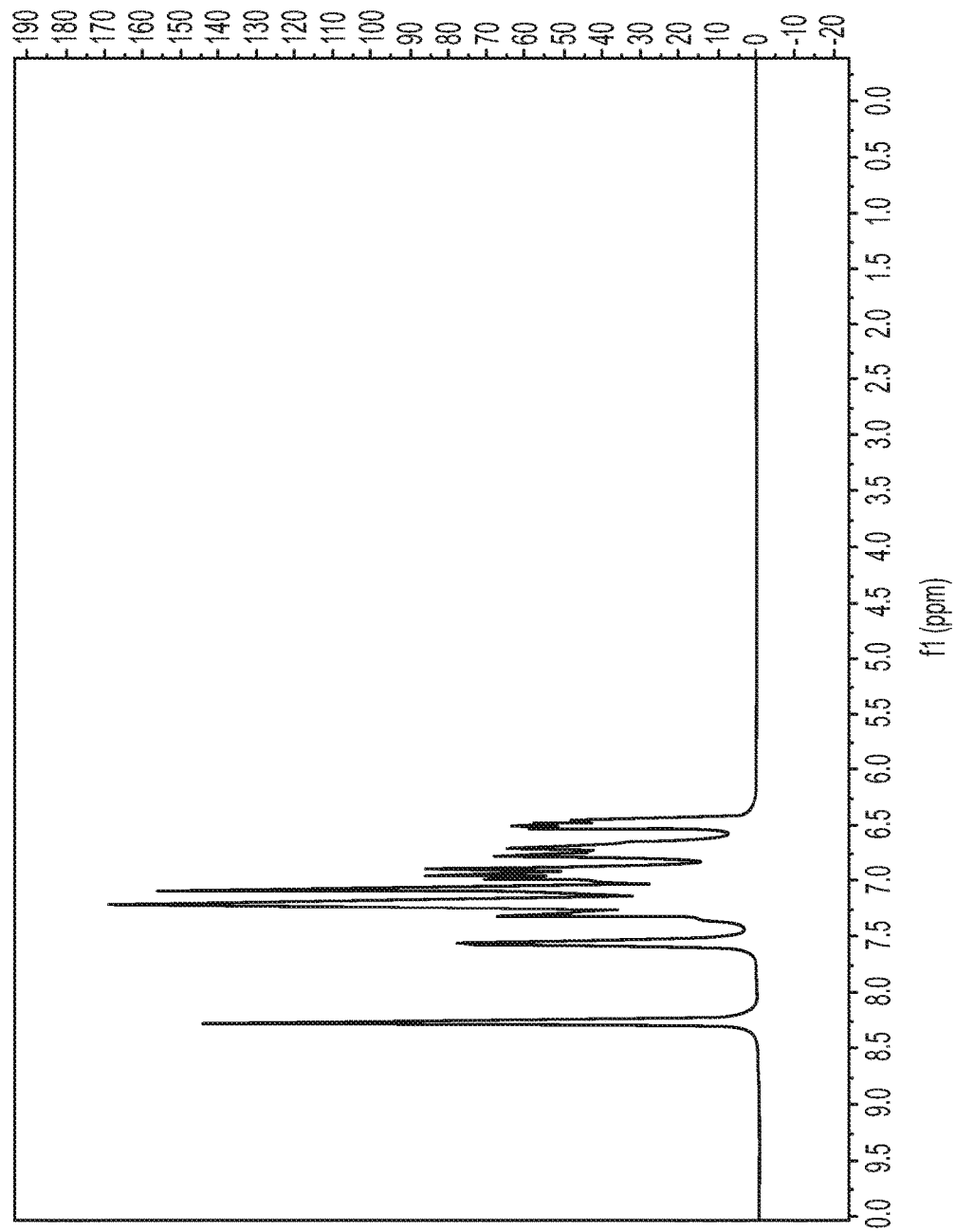
FIG. 1 is a nuclear magnetic resonance (NMR) spectroscopy spectrum of a chemical composition according to the embodiments shown and described herein.

Embodiments of the present disclosure generally relate to bis-Schiff bases. Specifically, embodiments of the present disclosure relate to chemical compositions, polymers produced from the chemical compositions, and chemical formulations, which comprise the structure of Formula (I):

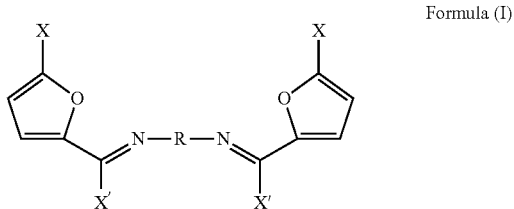

Formula (I)

where R is an aromatic moiety, and X and X' may both or independently comprise aromatic, aliphatic moieties, or a hydrogen. The aromatic moiety may be any suitable constituent containing a cyclic, ring-shaped functional group. The aliphatic moiety may be any saturated or unsaturated, straight or branched open-chain compound. In some embodiments, X, X', or both X and X' may be a hydrogen atom.

Any suitable aromatic moiety may be chosen for R, which may vary based on the desired application of use. In some embodiments, R may contain at least one of a phenyl group, a naphthyl group, an ether group, a sulfur group, a sulfonyl group, an imine group, an amide group, a methylene group, a dialkyl methylene group, an isopropyl group, a trifluoromethyl group, a hexafluoroisopropyl group, a carbonyl group, a benzyl group, or combinations of these. In some embodiments, R may be an aromatic moiety having the structure of at least one of Formula (II) or Formula (III):

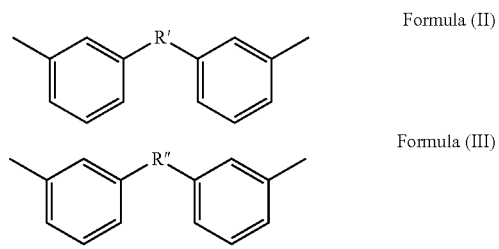

where R' and R" may be, for instance, an oxygen group, an imine group, an amide group, a methylene group, a dialkyl methylene group, an isopropyl group, a trifluoromethyl group, a hexafluoroisopropyl group, an ether group, a sulfonyl group, a sulfur group.

It should be understood that a "group" is used to refer to a moiety containing at least one atom. For instance, an "oxygen group" is used to refer to any moiety containing oxygen, such as a single oxygen atom or a complex arrangement containing one or many oxygen atoms. In any of the formulas depicted throughout this disclosure, an unconnected bond "—X" refers to an open covalent bond, which may be a single, double, or even a triple bond between that constituent and another molecule.

In some embodiments, R may contain one or more of Formula (IV), Formula (V), Formula (VI), Formula (VII), Formula (VIII), Formula (IX), Formula (X), Formula (XI), Formula (XII), Formula (XIII), Formula (XIV), Formula (XV), Formula (XVI), Formula (XVII), Formula (XVIII), Formula (XIX), Formula (XX), Formula (XXI), Formula (XXII), Formula (XXIII), Formula (XXIV), Formula (XXV), or Formula (XXVI):

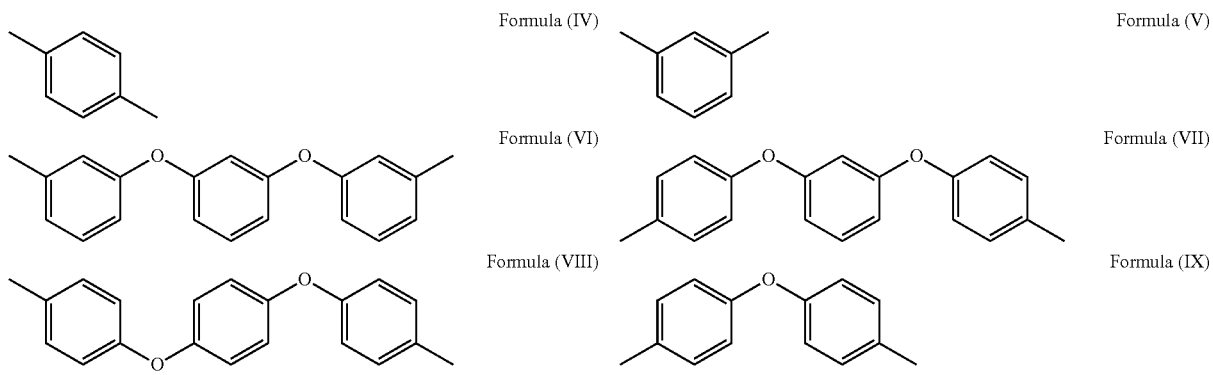

Formula (X)

Formula (XI)

Formula (XII)

Formula (XIII)

Formula (XIV)

Formula (XV)

Formula (XVI)

Formula (XVII)

Formula (XVIII)

Formula (XIX)

Formula (XX)

Formula (XXI)

Formula (XXII)

Formula (XXIII)

Formula (XXIV)

Formula (XXV)

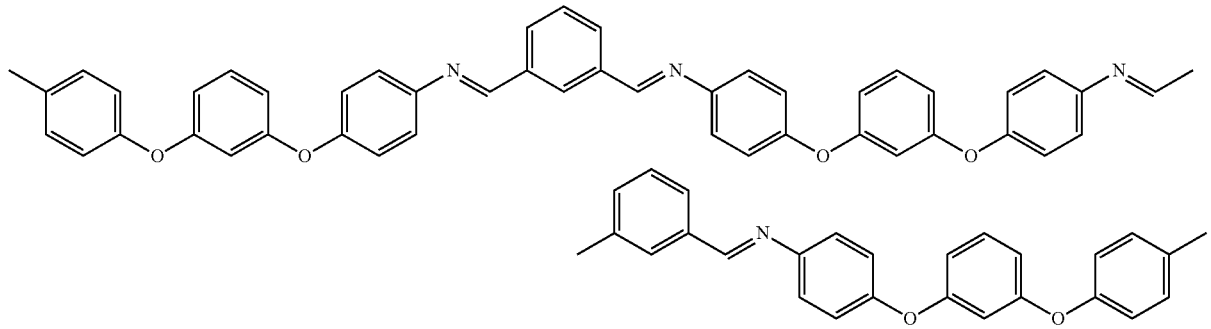

Formula (XXVI)

In some embodiments, the chemical composition may be a neat polymerizable resin. In some embodiments, the chemical composition may contain a monomer having the structure of Formula (I) with less than or equal to 5 wt % of fillers, reinforcements, pigments stabilizers, or additives, based on the total weight of the resin. In some embodiments, the chemical composition may contain only a monomer having the structure of Formula (I) with less than or equal to 3 wt %, less than 2 wt %, or less than 1 wt % of fillers, reinforcements, pigments stabilizers, or additives, based on the total weight of the resin. In some embodiments, the chemical composition may not contain, or may not contain more than trace amounts of fillers, reinforcements, pigments stabilizers, or additives.

In some embodiments, the chemical composition may be produced by reacting an aromatic diamine with a heterocyclic compound having at least one carbonyl moiety. The carbonyl moiety may be an aldehyde or a ketone functional group. In some embodiments, the structure of the heterocyclic compound may comprise Formula (XXVII).

Formula (XXVII)

where X and X' may both or independently comprise aromatic moieties, aliphatic moieties, or a hydrogen. In some particular embodiments, X may comprise an aromatic or aliphatic moiety and X' may be a hydrogen. In some particular embodiments, X may comprise a methyl, a propyl, a dimethylamino, boronic acid, a naphthyl, a phenyl, a 4-cyanophenyl, a (1-(5-(1-(5-Formyl-2-furfyl)-1-methylethyl)-2-furfyl)-1-methylethyl) moiety, or combinations thereof, and X' may be a methyl group or a hydrogen.

Without being bound by any particular theory, the two amine groups may react with the heterocyclic compound to produce a bis-Schiff base compound having two heterocyclic moieties bonded at opposite ends of the structure through the two Schiff-base moieties, as depicted in Formula (I).

In some particular embodiments, the heterocyclic compound may include furfural, 5-methylfurfural, 5-(1-(5-(1-(5-Formyl-2-furfyl)-1-methylethyl)-2-furfyl)-1-methylethyl)-2-furaldehyde, 5-Propyl-furan-2-carbaldehyde, 5-(Dimethylamino)-2-furaldehyde, 5-Formyl-2-furanylboronic acid, 5-(1-naphthyl)-2-furaldehyde, 4-(5-formyl-furan-2-yl)benzonitrile, 3-Furancarboxaldehyde, or combinations thereof.

The aromatic diamine may include at least one phenyl group, ether group, sulfonyl group, hydrocarbyl group, or combinations thereof. In some embodiments, the aromatic diamine may comprises the formula: $NH_2$—$R^3$—$NH_2$ in which $R^3$ includes one or more of Formula (IV), Formula (V), Formula (VI), Formula (VII), Formula (VIII), Formula (IX), Formula (X), Formula (XI), Formula (XII), Formula (XIII), Formula (XIV), Formula (XV), Formula (XVI), Formula (XVII), Formula (XVIII), Formula (XIX), Formula (XX), Formula (XXI), Formula (XXII), or Formula (XXIII), as previously described. For instance, aromatic diamine, $NH_2$—$R^3$—$NH_2$, may include 4,4'-(1,3-phenylenedioxy)dianiline, 1,3-bis(3-aminophenoxy)benzene, 4,4'-oxydianiline, 4-aminophenyl sulfone, 3-aminophenyl sulfone, isophthalaldehyde derivatives, or combinations thereof.

Without being bound by any particular theory, the chemical composition may have improved rheological properties, such as, for instance, viscosity stability and melt viscosity. In some embodiments, the chemical composition may have a viscosity of less than or equal to 100,000 centipoises (cP) (i.e., 100 Pascal-seconds (Pa·s)) at temperatures of from 60° C. to 150° C. for at least 4 hours. The chemical composition may have a melt viscosity that is relatively stable between 60° C. and 170° C., which may indicate that the chemical composition is not curing or crosslinking or has a very slow curing rate below 170° C. In some embodiments, the chemical composition may have a viscosity of less than or equal to 100,000 cP at temperatures of from 100° C. to 150° C., from 100° C. to 120° C., from 120° C. to 150° C., from 60° C. to 170° C., or from 60° C. to 120° C. for at least 4 hours, for at least 3 hours, for at least 2 hours, for at least 1 hour, for at least 5 hours, or for at least 6 hours. For instance, in some embodiments, the chemical composition may have a viscosity of between 100 cP and 750 cP for at least 4 hours at 120° C. The chemical composition may have a viscosity of between 100 cP and 750 cP, 250 cP and 600 cP, or 300 cP and 500 cP for at least 4 hours at 120° C. In some embodiments, the chemical composition may have a melt viscosity of less than or equal to 100,000 cP at less than or equal to 150° C., as measured by rotation rheometry. In some particular embodiments, the chemical composition may even have a melt viscosity of less than or equal to 500 cP at less than or equal to 150° C., as measured by rotation rheometry.

Again, without being bound by any particular theory, this may allow for at least 4 hours at which the chemical composition has a workable viscosity without undergoing gelation or otherwise further reacting, which may cause the composition to become un-processable. This may create a greater processing window (both in terms of time and temperature) upon which the chemical composition is malleable and may be, for instance, processed into a polymer or polymer composite. The reaction rate of the further reactions, such as polymerization, crosslinking, and/or curing, may occur at a slower rate than conventional resins.

In some embodiments, the chemical composition may have a low viscosity, such as below about 100,000 cP at temperatures below 170° C. The viscosity may be measured by rotational rheometry by acquiring viscosity versus temperature curves on a parallel plate rheometer, commercially available from TA Instruments (New Castle, Del.) at a controlled strain of 0.01% and an angular frequency of 10.00 radians per second (rad/s) by heating samples at a rate of 2° C. per minute to the isothermal temperature specified. In one or more embodiments, the chemical composition may have a melt viscosity of less than or equal to 500 cP at 125° C. as measured by rotation rheometry. In one or more embodiments, the chemical composition may have a melt viscosity of less than or equal to 100,000 cP at 125° C. as measured by rotation rheometry. For instance, the chemical composition may have a melt viscosity of from 10,000 to 100,000 cP, from 40,000 to 80,000 cP, or from 20,000 to 50,000 cP at 125° C. In some particular embodiments, the chemical composition may have an extremely low viscosity at less than 200° C., such as less than 500 cP. In some particular embodiments, the chemical composition may have a melt viscosity of from 100 to 500 cP, from 200 to 400 cP, or from 300 to 500 cP at 125° C.

Embodiments of the disclosure additionally relate to chemical formulations produced by dissolving the chemical composition in at least one solvent. In certain applications, such as using the chemical composition as a material to produce thin film or coating on a panel or fabric, it may be advantageous to add solvent to the chemical composition to dilute the solution before applying the chemical composition via a coating or spray painting process to facilitate fast drying of the resulting film or coating. In some instances, the addition of solvent to the chemical composition can impart desirable properties, such as a tackiness or a plasticizing effect, to the chemical composition in order to make certain type of products, for instance a polymer composite prepreg. The chemical composition may be in accordance with any of the embodiments previously described. Dissolution may include any suitable techniques known in the art, including but not limited to mixing, stirring, or otherwise agitating the formulation, with or without the application of heat.

Many solvents may be suitable for use in the chemical formulation. The solvent may be any substance that allows the chemical composition to become incorporated into the solvent as a solute. The solvent may, in some embodiments, be used to achieve a particular viscosity based on the desired application of use. In some embodiments, the solvent may be toluene, dichloromethane, chloroform, acetone, tetrahydrofuran, cyclopentanone, parachlorobenzotrifluoride, dibasic ester, N-methylpyrrolidine, and combinations thereof. In some particular embodiments, the solvent may contain parachlorobenzotrifluoride. In some embodiments, parachlorobenzotrifluoride may be used to provide solubility without the use of volatile organic compounds (VOCs), which can pose environmental and health hazards.

Various amounts of the solvent are contemplated based on numerous factors, such as, for instance, the solubility of the chemical composition in the solvent and the relative strength of the solvent. The strength of the solvent may be determined based on the relative polarity of the solvent with respect to the chemical composition, which is related to the interaction of the composition with a solvent leading to the stabilization of the chemical composition in solution. In some embodiments, the chemical formulation may contain from 10 weight percent (wt %) to 90 wt % of the chemical composition, as measured based on the total weight of the chemical formulation. The chemical formulation may contain from 20 wt % to 90 wt %, 30 wt % to 90 wt %, from 40 wt % to 90 wt %, from 50 wt % to 90 wt %, from 60 wt % to 90 wt %, or from 70 wt % to 90 wt % of the chemical composition. In some embodiments, the chemical formulation may contain from 30 wt % to 85 wt %, from 40 wt % to 60 wt %, from 30 wt % to 50 wt %, from 40 wt % to 70 wt %, or from 50 wt % to 85 wt % of the chemical composition based on the total weight of the chemical formulation.

In some embodiments, the chemical formulation may contain a ratio of 1 part of the chemical composition to 2 parts of solvent, or a 1:2 ratio. In other embodiments, the chemical formulation may contain from a 1:2 to a 1:10 ratio, such as from a 1:2 to a 1:5 ratio, a 1:2 to a 1:4 ratio, or a 1:2 to 1:3 ratio. In some embodiments, particularly in which the solvent is strong, the chemical formulation may contain from a 10:1 to a 1:2 ratio, such as from a 10:1 to a 1:1 ratio, from a 10:1 to a 5:1 ratio, from a 10:1 to a 4:1 ratio, from a 2:1 to 3:1 ratio, or from a 10:1 to 8:1 of chemical composition to solvent.

In some embodiments, the chemical composition, the chemical formulation, or both, may be used to produce a polymer or a polymer composite. As a non-limiting example, a chemical composition in which R is in accordance with Formula (VII) may be thermally polymerized in a mold at 220° C. for 4 hours to produce a thermosetting polymer that has a glass transition temperature of 154° C. with a storage modulus of 3.1 gigapascals (GPa) at room temperature.

In some embodiments, the polymer composite may be a fiber reinforced composite, or it may be a particulate-reinforced composite. The chemical composition, and its resulting polymer or polymer composite may be used or may be formulated for use in many industries. For example, the composite may be used in the architecture, construction, oil and gas, mining, space, aerospace, defense, automotive, marine, or manufacturing industries. In other embodiments, the chemical composition, and its resulting polymer or polymer composite may be used in chemical, coating, pharmaceutical, apparel, or electronic industries.

The polymer produced from the present disclosure of chemical composition may, in some embodiments, not only have improved thermal and electronic qualities, and may also have advantageous mechanical properties as well. In some embodiments, the polymer may have a storage modulus of greater than or equal to 2 GPa, as measured according to the American Society for Testing and Materials (ASTM) Standard D4065. For instance, the polymer may have a storage modulus of from 2 to 4 GPa, such as from 1 to 3 GPa, or from 2 to 3 GPa, or from 3 to 4 GPa.

In some embodiments, due in part to these improved properties, the chemical composition, may be useful in a variety of industrial applications. In some embodiments, the chemical composition the polymer or the polymer composite made from it, or both, may be used in the architecture, coating, composite, construction, oil and gas, mining, defense, space, aerospace, automotive, marine, manufacturing, pharmaceutical, or electronic industries. In some particular embodiments, the chemical composition, or the polymer made from it may be used as chelating agents for use in chemical sensors to detect presence of metal ions in solutions, such as Ag(II), Cu(II), Fe(II) or Zn(II), Co(II), Hg(II), Ni(II), Pb(II), due to their abilities to form ion complexes with these ions. In another embodiment, the chemical composition or the polymer made from it, may be used in the making of catalyst for chemical synthesis by complexing with metal ions, such as Ag(II), Cu(II), Fe(II) or Zn(II).

In other embodiments, the chemical composition, or the polymer made from it, may be used to produce antifungal, antibacterial or antiviral agents in pharmaceutical industry. In other embodiments, the chemical composition, with or without solvent, or the polymer made from it, may be used in the clothing industry to treat fabric, apparel to provide antifungal, antibacterial or antiviral properties. In other embodiments, the chemical composition or the polymer made from it, may be used as anti-corrosion agents due to the presence of the imine group, to prevent corrosion of metals such as steel, copper, aluminum, and zinc In other embodiments, the chemical composition, the polymer made from it, or both, may be used in electronic industries, for instance, in optical computers, imaging systems, organic or lithium batteries, as photostabilizers, optical memory storage, circuit board substrate, and as housing materials for electronic devices. In some other particular embodiments, the chemical composition may be used in making of neat polymer, fiber-reinforced polymer composite, or particulate-reinforced polymer composite panel, parts, or structures for architecture, building construction, coating, composite, mining, oil and gas, space, aerospace, automotive, marine industries.

Examples

The various embodiments of the chemical compositions, formulations, and composites will be further clarified by the following examples. The examples are illustrative in nature, and should not be understood to limit the subject matter of the present disclosure. To further illustrate the chemical properties of the chemical compositions and formulations of the present embodiments, experimental data was obtained on two particular embodiments of the chemical compositions of the present disclosure.

Referring now to the Figures, FIG. 1 is a nuclear magnetic resonance (NMR) spectroscopy spectrum of one embodiment of the chemical composition, Example 1. Example 1 is a chemical composition having the formula: $C_{28}H_{20}N_2O_4$, where R is in accordance with Formula VII. The chemical structure of Example 1 is:

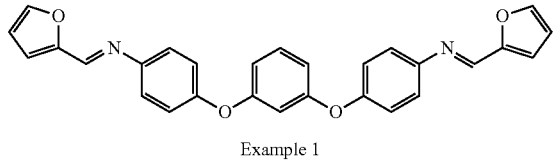 [SMILES: C(=N\c1ccc(Oc2cccc(Oc3ccc(/N=C/c4ccco4)cc3)c2)cc1)/c1ccco1]

Example 1

Example 1 was prepared by equipping a 2 liter (L) three-neck flask with a mechanical stirrer and charging the center neck with 408.6 grams (g) of furfural. One neck was sealed with a septum and the mixer was set to 200 rotations per minute (RPMs) and 603.4 g of 4,4'-(1,3-Phenylenedioxy)dianiline was added through the remaining neck. The addition took place over a span of 20 minutes, after which the remaining neck was sealed with a septum. Upon the dissolution of the solid material, the flask was heated to 100° C. using an oil bath and mixing was allowed to continue for 1 hour. A vacuum adaptor was attached to one neck of the reaction vessel and the water produced by the reaction was removed in vacuo. The desired material was cooled and characterized by gas chromatography-mass spectrometry (GC/MS) and proton nuclear magnetic resonance spectroscopy ($^1$H NMR). Example 1 obtained a yield of greater than 90%.

The NMR spectrum details are as follows: $^1$H NMR (82 MHz, CDCl$_3$) δ 8.24 (s, 2H), 7.54 (d, J=1.8 Hz, 2H), 7.22 (dt, J=7.3, 2.7 Hz, 5H), 7.05 (d, J=2.4 Hz, 3H), 6.90 (d, J=3.5 Hz, 2H), 6.74 (m, 4H), 6.48 (dd, J=3.5, 1.8 Hz, 2H). Mass Spectrum Calc. 448.4 Found 448.4. The above data confirms the structure of the compound.

Without being bound by any particular theory, the physical properties of a polyphenyl ether (PPE), such as the chemical composition show in Example 1, may depend on the number of aromatic rings and the substitution pattern of those rings. PPEs that contain two and three benzene rings are typically solids at room temperature. The melting point however may be lowered if the PPE contains more meta-phenylene rings. Again, without being bound by any particular theory, it is believed the meta-substitution may lead to lower melting points or lower viscosities at the same temperature as compared to para-substituted compounds. Typically, PPEs with ortho- and para-substituted rings have the highest melting points.

Figure 2:
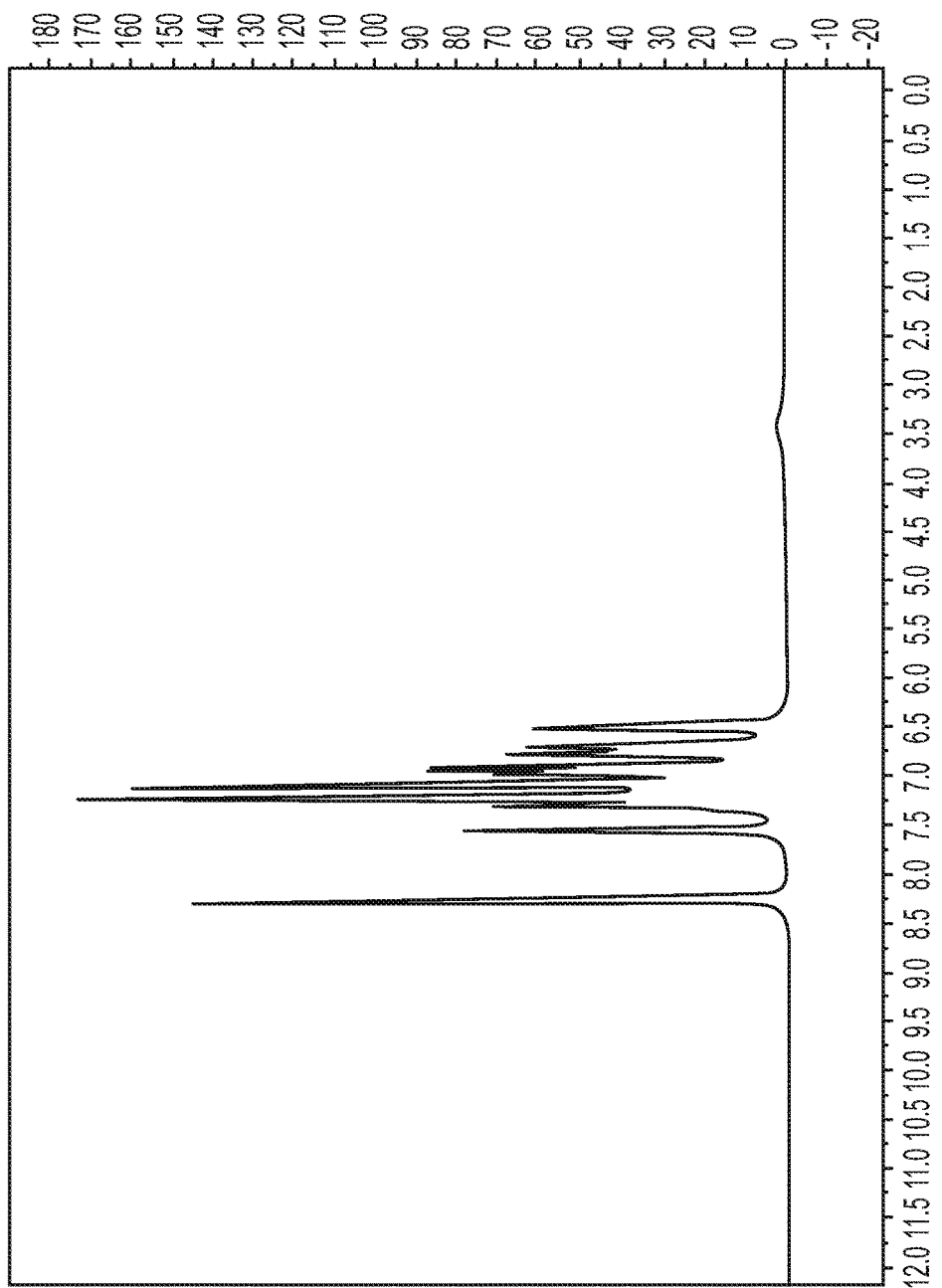
FIG. 2 is an NMR spectrum of another embodiment of a chemical composition according to the embodiments shown and described herein.

FIG. 2 is another NMR spectrum of another embodiment of the chemical composition having the formula $C_{28}H_{20}N_2O_4$, in which R comprises a structure according to Formula VI. The chemical structure of Example 2 is:

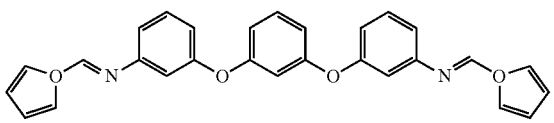

Example 2

Example 2 was prepared by equipping a 2 L three-neck flask with a mechanical stirrer and charging the center neck with 408.6 g of furfural. One neck was sealed with a septum and the mixer was set to 200 RPMs and 603.4 g of 1,3-Bis(3-aminophenoxy)benzene was added through the remaining neck. The addition took place over a span of 20 minutes, after which the remaining neck was sealed with a septum. Upon the dissolution of the solid material, the flask was heated to 100° C. using an oil bath and mixing was allowed to continue for 1 hour. A vacuum adaptor was attached to one neck of the reaction vessel and the water produced by the reaction was removed in vacuo. The desired material was cooled and characterized by GC/MS and $^1$H NMR. Example 2 obtained a yield of greater than 90%.

The NMR spectrum details are as follows: $^1$H NMR (82 MHz, CDCl$_3$) δ 8.25 (s, 2H), 7.54 (d, J=1.8 Hz, 2H), 7.13 (tdd, J=8.9, 5.7, 2.3 Hz, 8H), 6.90 (d, J=3.5 Hz, 2H), 6.74 (m, 4H), 6.48 (dd, J=3.5, 1.8 Hz, 2H). Mass Spectrum Calc. 448.4 Found 448.4. This confirms the structure of the compound. As previously mentioned, it is believed the meta-substitution may lead to lower melting points or lower viscosities at the same temperature as compared to para-substituted compounds.

Figure 3A:
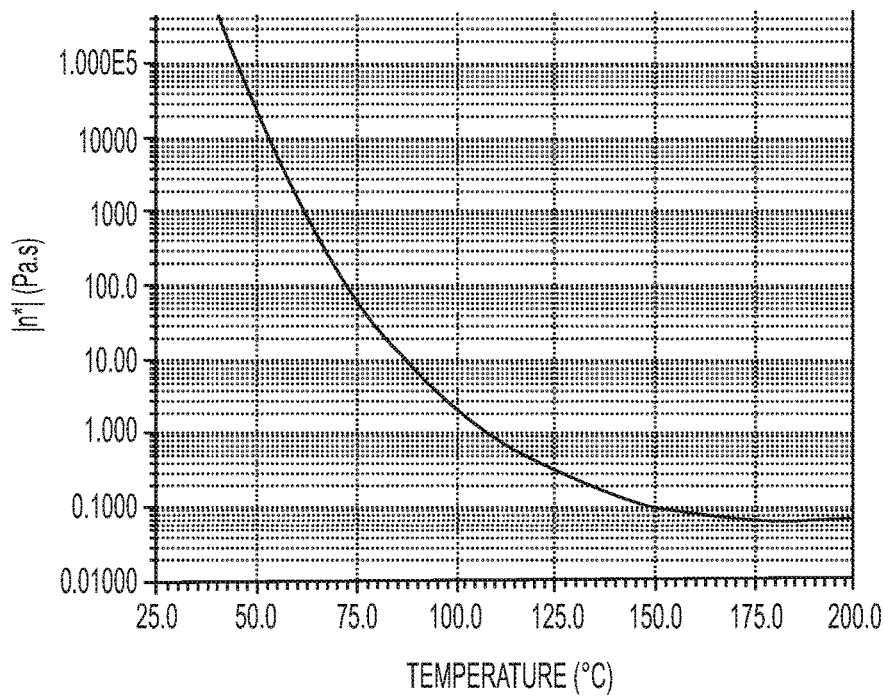
FIG. 3A is a viscosity versus temperature graph depicting the melt viscosity of an embodiment of a chemical composition according to embodiments shown and described herein.

FIG. 3A is a graph of the viscosity versus temperature depicting the melt flow viscosity of a chemical composition in accordance with the present embodiments, Example 1. In FIG. 3A, Example 1 was heated at a temperature ramp of 2° C. per minute using a TA instrument parallel plate rheometer at a controlled strain of 0.01% and an angular frequency of 10.00 rad/s. As shown in FIG. 3A, Example 1 exhibited a large drop in viscosity between room temperature and 100° C. as the composition melts, which levels and stabilizes between 150° C. and 200° C., indicating that the composition is not curing below 200° C. (rapid rising would indicate the composition is curing or otherwise further reacting). FIG. 3A also shows that Example 1 had a low viscosity over a large temperature range of up to a temperature of at least 200° C., leaving an ample temperature processing window in which Example 1 had a viscosity of about less than 1000 cP (1 Pa·s).

Figure 3B:
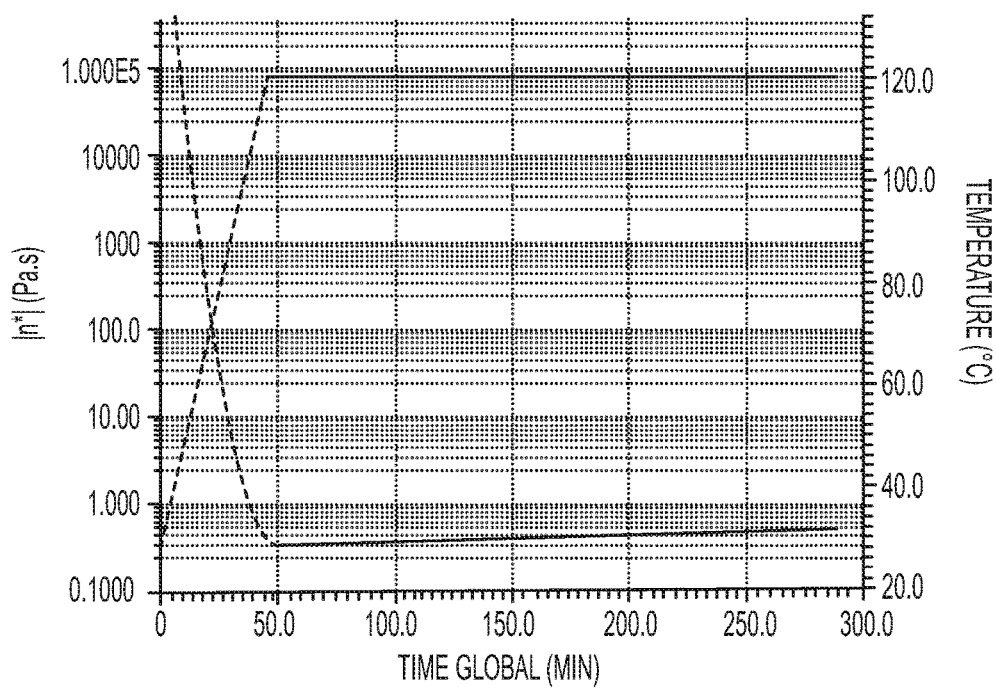
FIG. 3B is a viscosity versus time and temperature graph depicting the stability of an embodiment of a chemical composition according to embodiments shown and described herein.

FIG. 3B is another graph of viscosity versus temperature and time, showing the stability of the chemical composition of Example 1. The viscosity versus temperature curves were acquired on a TA instruments parallel plate rheometer at a controlled strain of 0.01% and an angular frequency of 10.00 rad/s. Samples were heated at a rate or 2° C. per minute to the isothermal temperature of 120° C. FIG. 3B shows Example 1 during a 4 hour dwell at 120° C. As shown, Example 1 was stable between 150 cP to 200 cP for a period of time of at least 4 hours. Example 1 was able to maintain a low melt flow viscosity for long periods without undergoing further reactions or showing signs of a significant increase in viscosity or temperature. This may allow for an extremely desirable working processing window or "pot life" in which Example 1 may be used in a variety of composite fabrication processes due to the improved workability, handling, and processing caused by the low viscosity over a long time period.

Figure 4A:
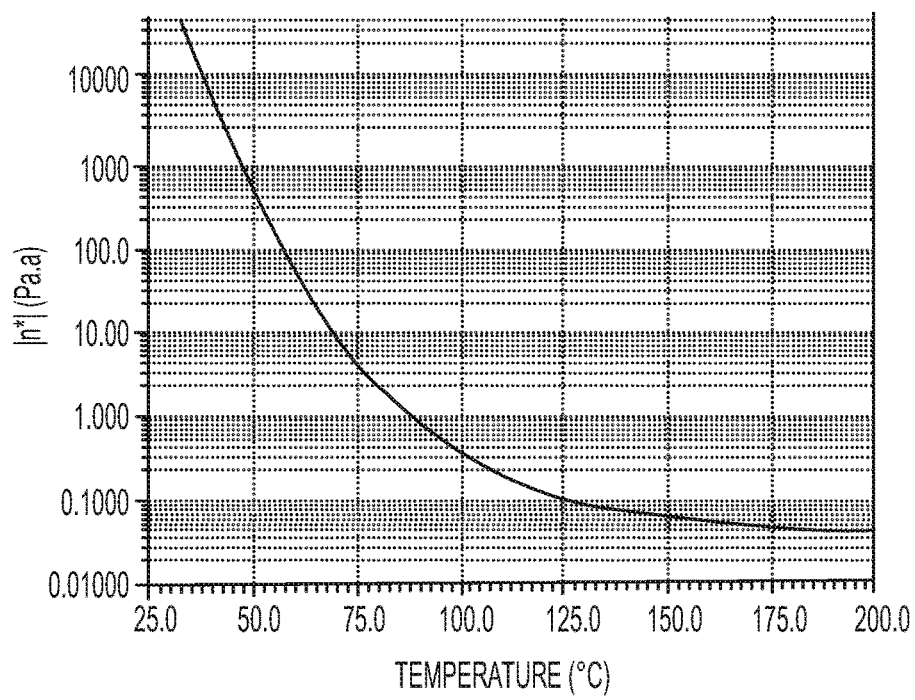
FIG. 4A is a viscosity versus temperature graph depicting the melt viscosity of another embodiment of a chemical composition according to embodiments shown and described herein.

Similarly, FIG. 4A is another viscosity versus temperature graph of a chemical composition in accordance with the present embodiments, Example 2. In FIG. 4A, Example 2 was again heated at a temperature ramp of 2° C. per minute. Like Example 1, Example 2 has a large drop in viscosity between room temperature and 100° C., which levels between 150° C. and 200° C., indicating that the composition did not exhibit significant curing below 200° C. within the experimental time frame. Again, Example 2 exhibits low viscosity over a large temperature range of up to a temperature of at least 200° C., leaving an ample temperature processing window (from at least about 100° C. to 200° C.) in which Example 2 had a viscosity of about less than 1000 cP.

Figure 4B:
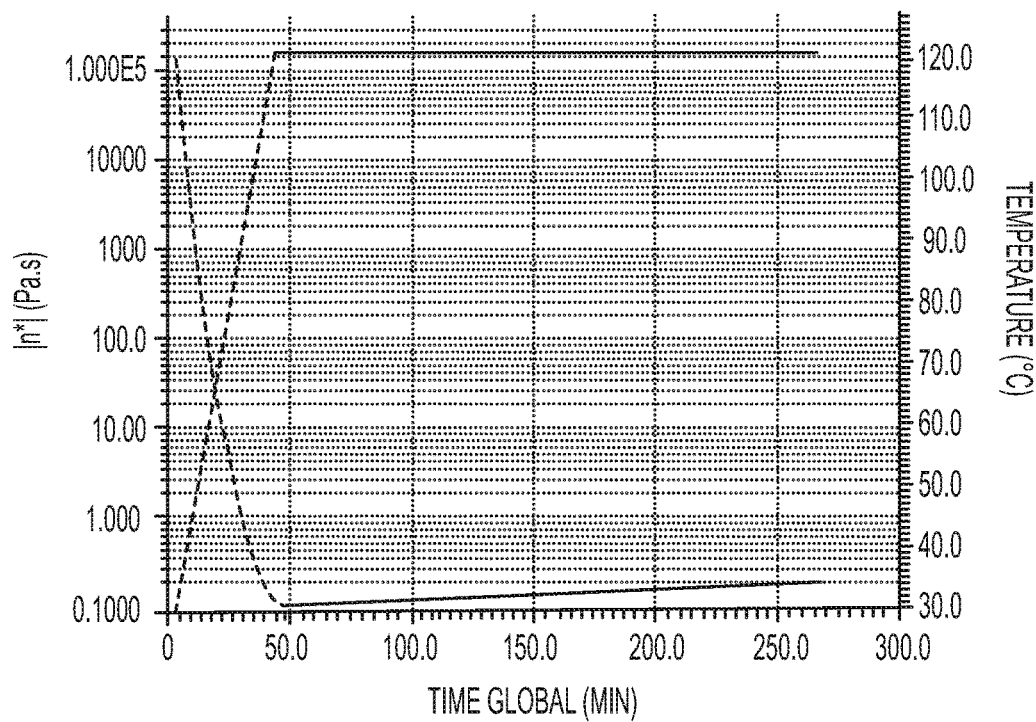
FIG. 4B is a viscosity versus time and temperature graph depicting the stability of an embodiment of a chemical composition according to embodiments shown and described herein.

FIG. 4B is another viscosity versus temperature and time graph showing the stability of the chemical composition of Example 2. FIG. 4B shows Example 2 during a 4 hour dwell at 120° C. Again, Example 2 was stable between 150 cP and 200 cP for at least 4 hours. Example 2 was able to maintain a low melt flow viscosity without undergoing further reactions or showing signs of either a significant increase in viscosity or in temperature, showing improved workability over a range of up to at least 4 hours.

It should be apparent to those skilled in the art that various modifications and variations may be made to the embodiments described within without departing from the spirit and scope of the claimed subject matter. Thus, it is intended that the specification cover the modifications and variations of the various embodiments described within provided such modification and variations come within the scope of the appended claims and their equivalents.

As used throughout, the singular forms "a," "an" and "the" include plural referents unless the context clearly dictates otherwise. Thus, for example, reference to "a" component includes aspects having two or more such components, unless the context clearly indicates otherwise.

Having described the subject matter of the present disclosure in detail and by reference to specific embodiments thereof, it is noted that the various details disclosed within should not be taken to imply that these details relate to elements that are essential components of the various embodiments described within, even in cases where a particular element is illustrated in each of the drawings that accompany the present description. Further, it should be apparent that modifications and variations are possible without departing from the scope of the present disclosure, including, but not limited to, embodiments defined in the appended claims. More specifically, although some aspects of the present disclosure are identified as particularly advantageous, it is contemplated that the present disclosure is not necessarily limited to these aspects.

What is claimed is:

1. A chemical composition comprising the structure of Formula (I):

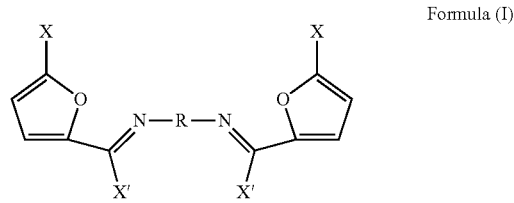

Formula (I)

wherein:
X consists of a hydrogen;
R is selected from at least one of Formula (IV), Formula (V), Formula (VI), Formula (VII), Formula (VIII), Formula (IX), Formula (X), Formula (XI), Formula (XII), Formula (XIII), Formula (XIV), Formula (XV), Formula (XVI), Formula (XVII), Formula (XVIII), Formula (XIX), Formula (XX), Formula (XXII), Formula (XXIII), Formula (XXIV), Formula (XXV), or Formula (XXVI);
X' comprises an aromatic moiety, an aliphatic moiety, or a hydrogen when R is selected from Formula (IV), Formula (V), Formula (VI), Formula (VII), Formula (VIII), Formula (XII), Formula (XIII), Formula (XIV), Formula (XV), Formula (XVI), Formula (XVII), Formula (XVIII), Formula (XIX), Formula (XX), Formula (XXII), Formula (XXIII), Formula (XXIV), Formula (XXV), or Formula (XXVI); and
X' consists of a hydrogen when R is selected from Formula (IX), Formula (X), or Formula (XI):

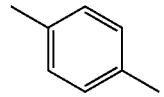

Formula (IV)

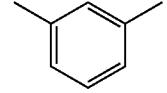

Formula (V)

Formula (VI)
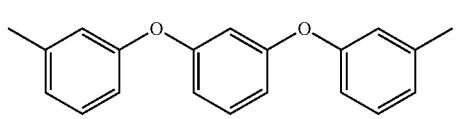
Formula (VII)
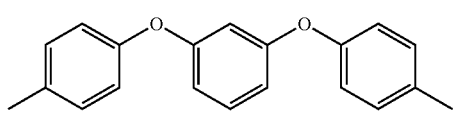
Formula (VIII)
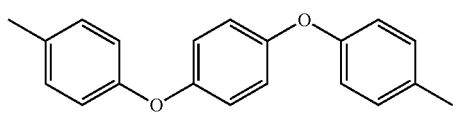
Formula (IX)
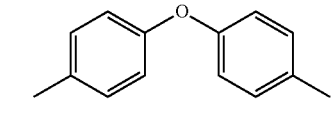
Formula (X)
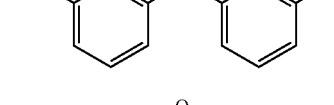
Formula (XI)
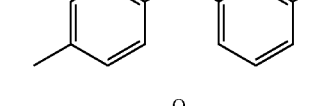
Formula (XII)
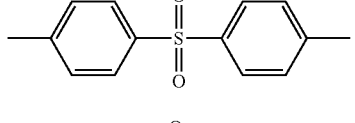
Formula (XIII)
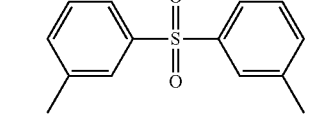
Formula (XIV)
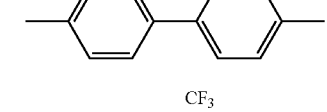
Formula (XV)
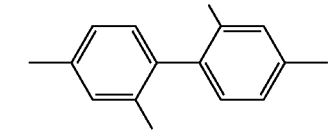
Formula (XVI)
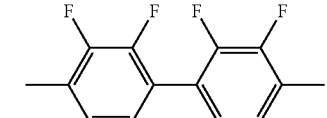
Formula (XVII)
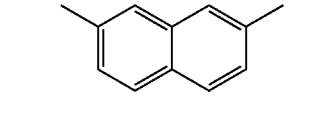
Formula (XVIII)
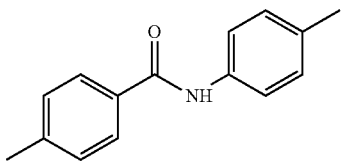
Formula (XIX)
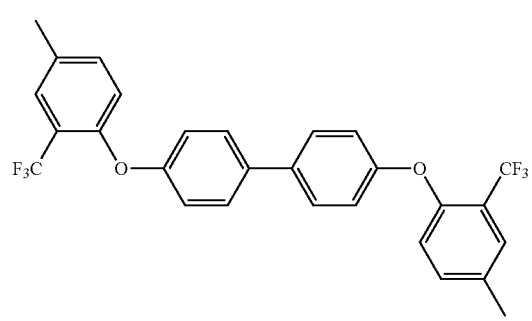
Formula (XX)
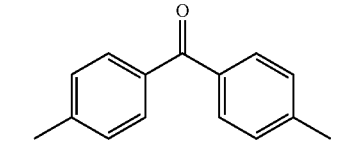
Formula (XXI)
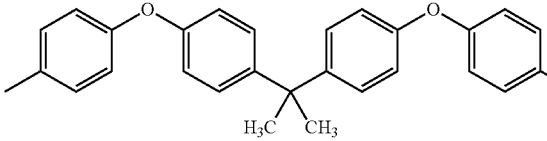
Formula (XXII)
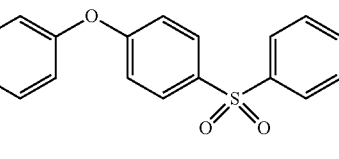
Formula (XXIII)
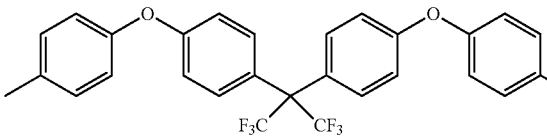
Formula (XXIV)
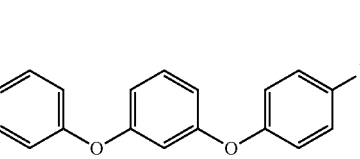
Formula (XXV)
Formula (XXVI)
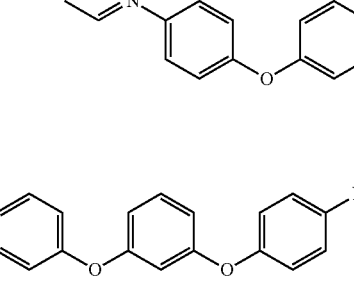

-continued

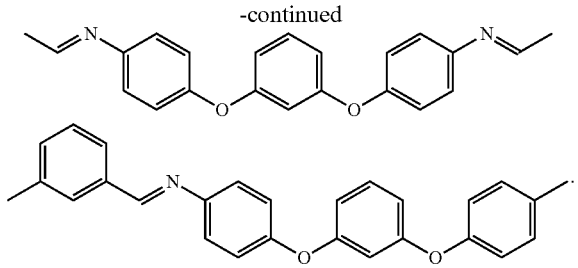

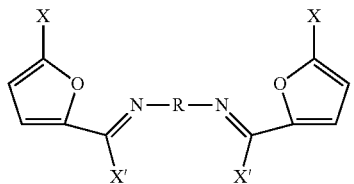

2. The chemical composition of claim 1, wherein the chemical composition has a melt viscosity of less than or equal to 100,000 centipoises (cP) at less than or equal to 150° C., as measured by rotation rheometry.

3. The chemical composition of claim 1, wherein the chemical composition has a melt viscosity of less than or equal to 500 cP at less than or equal to 150° C., as measured by rotational rheometry.

4. The chemical composition of claim 1, wherein the chemical composition is used in at least one of an architecture, coating, composite, construction, oil and gas, mining, defense, space, aerospace, automotive, marine, or electronic industries.

5. The chemical composition of claim 4, wherein the chemical composition is used as a thermosetting resin in the composite industry.

6. The chemical composition of claim 4, wherein the chemical composition is used as a thermosetting resin in the coating industry.

7. A chemical formulation comprising:
at least one solvent; and
a component having the structure of Formula (I):

Formula (I)

wherein:
X consists of a hydrogen;
R is selected from at least one of Formula (IV), Formula (V), Formula (VI), Formula (VII), Formula (VIII), Formula (IX), Formula (X), Formula (XI), Formula (XII), Formula (XIII), Formula (XIV), Formula (XV), Formula (XVI), Formula (XVII), Formula (XVIII), Formula (XIX), Formula (XX), Formula (XXII), Formula (XXIII), Formula (XXIV), Formula (XXV), or Formula (XXVI);
X' comprises an aromatic moiety, an aliphatic moiety, or a hydrogen when R is selected from Formula (IV), Formula (V), Formula (VI), Formula (VII), Formula (VIII), Formula (XII), Formula (XIII), Formula (XIV), Formula (XV), Formula (XVI), Formula (XVII), Formula (XVIII), Formula (XIX), Formula (XX), Formula (XXII), Formula (XXIII), Formula (XXIV), Formula (XXV), or Formula (XXVI); and
X' consists of a hydrogen when R is selected from Formula (IX), Formula (X), or Formula (XI):

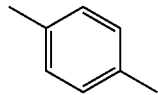
Formula (IV)

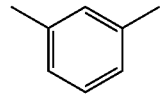
Formula (V)

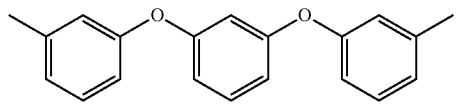
Formula (VI)

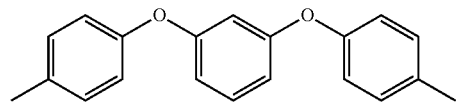
(Formula (VII))

Formula (VIII)

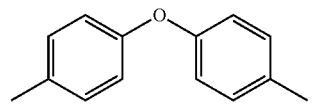
Formula (IX)

Formula (X)

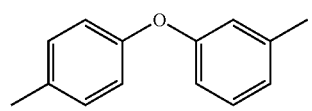
Formula (XI)

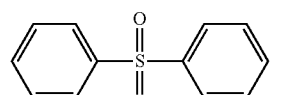
Formula (XIII)

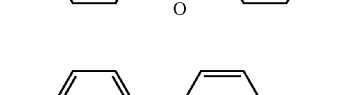
Formula (XIV)

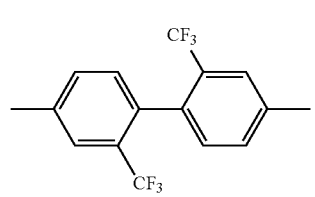
Formula (XV)

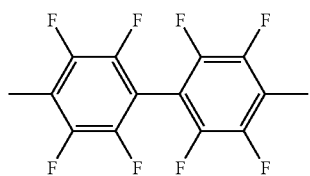

Formula (XVI)

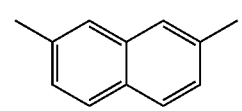

Formula (XVII)

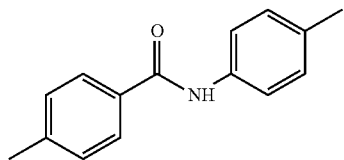

Formula (XVIII)

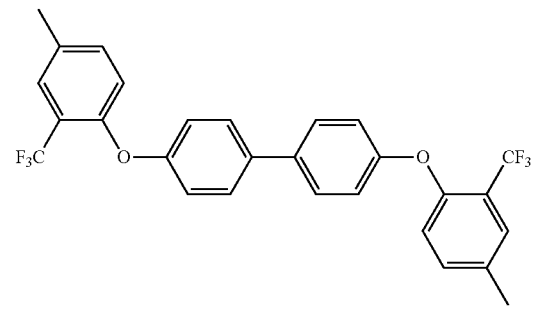

Formula (XIX)

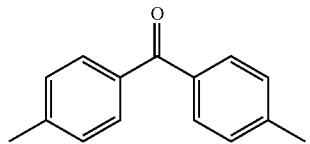

Formula (XX)

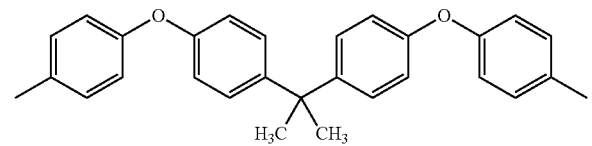

Formula (XXII)

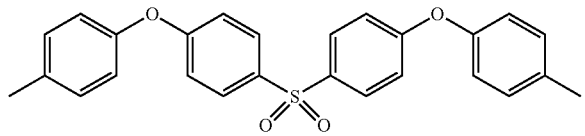

Formula (XXIII)

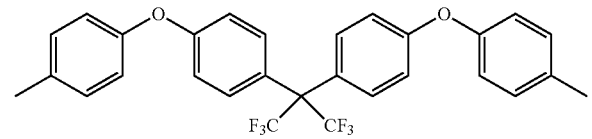

Formula (XXIV)

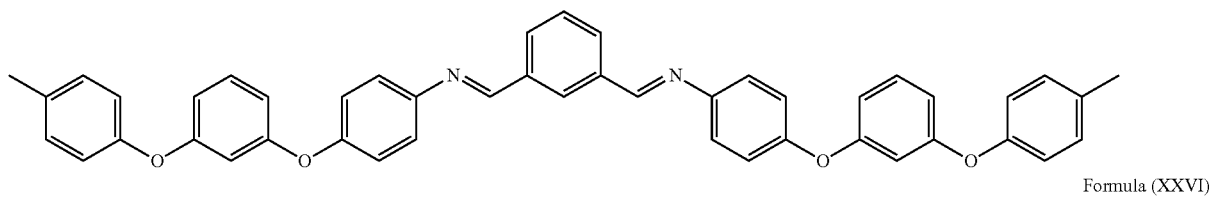

Formula (XXV)

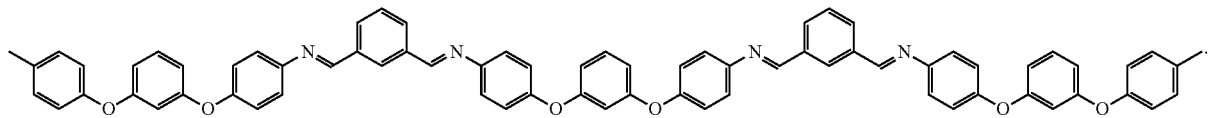

Formula (XXVI)

8. The chemical formulation of claim 7, wherein the solvent is selected from the group consisting of toluene, dichloromethane, chloroform, acetone, tetrahydrofuran, cyclopentanone, parachlorobenzotrifluoride, dibasic ester, N-methylpyrrolidine, and combinations thereof.

9. The chemical formulation of claim 7, wherein the chemical composition contains from 10 wt % to 90 wt % of the component having the structure of Formula (I).

10. The chemical formulation of claim 8, wherein the chemical composition contains from 40 wt % to 85 wt % of the component having the structure of Formula (I).

11. The chemical formulation of claim 7, wherein the formulation is used in at least one of an architecture, coating, construction, oil and gas, mining, defense, space, aerospace, automotive, marine, manufacturing, or electronic industries.

* * * * *